United States Patent
Karlberg et al.

(10) Patent No.: US 8,454,834 B2
(45) Date of Patent: Jun. 4, 2013

(54) COLUMN PACKING METHOD

(75) Inventors: Per Karlberg, Uppsala (SE); Erik Rurling, Bromma (SE); Joakim Svensson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 383 days.

(21) Appl. No.: 12/863,195

(22) PCT Filed: Jan. 15, 2009

(86) PCT No.: PCT/SE2009/000012
§ 371 (c)(1),
(2), (4) Date: Jul. 16, 2010

(87) PCT Pub. No.: WO2009/093953
PCT Pub. Date: Jul. 30, 2009

(65) Prior Publication Data
US 2011/0053127 A1    Mar. 3, 2011

(30) Foreign Application Priority Data
Jan. 23, 2008  (SE) .................................. 0800160

(51) Int. Cl.
*B01D 15/08*    (2006.01)
(52) U.S. Cl.
USPC .................... 210/656; 210/143; 210/198.2

(58) Field of Classification Search
USPC ......... 210/635, 656, 143, 198.2, 232; 141/12, 141/13, 80
See application file for complete search history.

(56) References Cited

U.S. PATENT DOCUMENTS

| | | | |
|---|---|---|---|
| 8,066,882 B2 * | 11/2011 | Edblad ......................... | 210/656 |
| 2003/0089662 A1 | 5/2003 | Hofmann | |
| 2007/0012626 A1 * | 1/2007 | Andersson et al. ........... | 210/656 |
| 2007/0090053 A1 * | 4/2007 | Windahl ....................... | 210/656 |
| 2007/0144955 A1 * | 6/2007 | Mann et al. .................. | 210/198.2 |
| 2010/0313992 A1 * | 12/2010 | Williams et al. .................. | 141/1 |

FOREIGN PATENT DOCUMENTS

| WO | WO 2007/045491 | 4/2007 |
|---|---|---|
| WO | WO 2008/109192 | 9/2008 |

* cited by examiner

*Primary Examiner* — Ernest G Therkorn

(57) ABSTRACT

A method for packing a media bed in a column (3). According to the invention the method comprises the steps of: providing data to a control unit (15) connected to the column (3), said data comprising at least a measured slurry concentration, a target bed height, a target packing factor or compression factor and minimum and maximum acceptable values for at least one of target bed height and target packing or compression factor; forcing a movable adapter (9) along a longitudinal axis of the column (3) in order to pack the media; detecting when the media bed is consolidated; the control unit (15) processing the provided data and the information about the consolidated bed height in order to present to the user acceptable bed heights, if there are any, giving acceptable packing or compression factors.

6 Claims, 5 Drawing Sheets

COLUMN PACKING METHOD

CROSS-REFERENCE TO RELATED APPLICATIONS

This application is a filing under 35 U.S.C. §371 and claims priority to international patent application number PCT/SE2009/000012 filed Jan. 15, 2009, published on Jul. 30, 2009, as WO 2009/093953, which claims priority to patent application number 0800160-4 filed in Sweden on Jan. 23, 2008.

FIELD OF THE INVENTION

The present invention relates to a media packing system for columns and media packing methods for use in columns. More specifically, the invention relates to methods for improving the quality, ease and consistency of packing chromatography media into chromatography columns.

BACKGROUND OF THE INVENTION

Columns used in liquid chromatography typically comprise a tubular body enclosing a packed bed of porous chromatography medium through which a carrier liquid flows, with separation taking place by material collection between the carrier liquid and solid phase of the porous medium. Typically, the medium is enclosed in the column as a packed bed formed by consolidating a suspension of discrete particles, known as slurry that is pumped, poured, or sucked into the column. Consolidation of the slurry into a consolidated packed bed is achieved by compressing the slurry so that it is packed into a volume, which is less than the volume that it would have occupied if it had been allowed to settle under the influence of gravity to form a sedimented bed. The efficiency of subsequent chromatographic separation relies strongly on 1) the liquid distribution and collection system at the fluid inlet and outlet of the packed bed, 2) on the special orientation (also know as the packing geometry) of the media particles in the packed bed, and 3) on the compression of the packed bed. If the compression of the packed bed is too low then chromatographic separations performed on that bed suffer from "tailing" and, generally, such insufficiently compressed beds are unstable. If the compression of the packed bed is too high then chromatographic separations performed by the bed suffer from "leading" and such over-compressed beds can affect throughput and binding capacity, and, in general, give much higher operating pressures. If the compression is optimum, then the separation peaks formed during use exhibit much less leading or tailing and are substantially symmetrical. The optimum degree of compression required for a column is determined experimentally for each column size (width or diameter), bed height, and media type.

Prior to any separation process, the bed has to be prepared by starting from the slurry of particles that has to be introduced into the column. The process of bed formation is called 'the packing procedure' and a correctly packed bed is a critical factor influencing the performance of a column containing a packed bed. One of the primary goals of the packing procedure is to provide a bed, which is compressed by the optimum amount of compression, i.e. the optimum compression factor. The height of the bed which often is user defined when it is optimally compressed is called the target compressed bed height.

Large-scale columns, are preferably prepared by injecting into the column a predetermined volume of slurry having a specified concentration of media particles. Once the predetermined volume of slurry has been delivered into the column it needs to be further consolidated and compressed by moving a movable adapter down the longitudinal axis of the column towards the bottom of the column, normally at a constant speed. The excess liquid during this procedure is expelled at the column outlet, while the media particles are retained by means of a filter material, a so-called 'bed support', with pores too small to allow the media particles to pass though. The packing process is complete once the packed bed has been compressed by the optimum degree of compression. The packing process is considered successful if the compressed bed allows for a good and robust chromatographic performance. However, packing such an optimally compressed bed of chromatography media in a chromatography column by manual means is not easy to accomplish in practice due to the fact that the quality of the final packed bed depends to a great extent on the skill of the operator. During filling and subsequent packing of the column, the operator manually selects and adjusts all packing parameters such as valve positions, pump speed, adapter's speed of movement, etc. The operator has to measure the slurry concentration in order to decide how much slurry that should be filled into the column. If the measure of the slurry concentration is not exact (which is often the case because it is hard to measure the slurry concentration exactly) the volume of the slurry filled into the column is not optimal and the consolidated bed will settle at a bed height that was not expected (as calculated from the measured slurry concentration) and hereby the target packing factor can not be achieved at target bed height. Furthermore, the operator also has to judge the point when the adapter starts compressing the bed. This point is used to calculate how much further the adapter must move in order to obtain the required amount of compression. Mistakes in the selection of any of the packing parameters normally lead to a poorly performing column. Further, in columns equipped with a transparent tube it may be difficult, and in columns equipped with a non-transparent tube such as stainless steel it is impossible, to judge by eye when compression of the bed actually starts and a significant error at this point makes it impossible to obtain an optimally compressed bed.

There is also a risk of damaging the media and the column if the user takes wrong decisions.

Therefore, there is a need for a system and method for the accurate and reproducible packing of chromatography media into chromatography columns. To repack a wrongly packed column is both time consuming and costs a lot of money.

SUMMARY OF THE INVENTION

An object of the invention is to provide a column packing system and a method for packing media into columns in order to overcome the drawbacks of the prior art systems.

A further object of the invention is to provide a column packing method and system giving an acceptable packing factor to the compressed bed at acceptable bed height.

This is achieved in a method according to claim 1.

Hereby the user will be presented different acceptable bed heights together with their expected, acceptable packing or compression factors.

Suitably windows in time or distance as to when to stop the packing such that both bed height and pack factor are within given acceptable ranges are presented to the user. Hereby the user can easily see the different options of when to stop the packing.

Preferably a warning is presented to the user if no acceptable bed height values can be achieved or if the user has not stopped the packing after the minimum acceptable bed height has passed. Hereby damage of the media and/or the column can be prevented.

Suitably the method further comprises controlling the packing to be automatically stopped after a predetermined period of time if no acceptable bed height values can be achieved or if the user has not stopped the packing after the minimum acceptable bed height has passed. Hereby damage of the media and/or the column can be prevented.

DETAILED DESCRIPTION OF THE INVENTION

The presently preferred embodiments of the invention are described with reference to the drawings. The descriptions of the preferred embodiments are exemplary and are not intended to limit the scope of the invention.

As used herein and in the appended claims:

The term "column" is intended to include the terms "vessel" and "cell", as well as any other structure utilized by practitioners of the separation arts, to effect a separation, and/or reaction, and/or catalyzation, and/or extraction of components from an admixture by bringing the admixture into contact with solid or liquid exchange media, known as the packed bed.

The term "slurry" is a dispersion of media particles and liquid.

The term "longitudinal direction of flow" refers to the direction of flow from an inlet towards an outlet within a column "Longitudinal" is used consistently to designate the dominant flow path of fluid through a cell without regard to direction.

The term "distribution system" refers to structures through which fluids are introduced to a column and the term "collection system" refers to structures used to collect fluids from a column.

The term "sedimented bed height" refers to the height of a bed of media particles which is obtained when a bed is formed after the media particles in a slurry are allowed to sediment under the influence of gravity only—such a bed is called a "sedimented bed".

The term "consolidated bed height" refers to the height of a bed of media particles that is obtained when a bed is formed in a column while the media particles in a slurry are forced to sediment when a flow of fluid is applied through the column in the longitudinal direction of flow either by 1) pumping liquid into the column, 2) by pumping liquid out of the column, or 3) by the movement (for example, the descent) of a movable adapter, which forces liquid out of the column—such a bed is called a "consolidated bed".

The term "compressed bed height" refers to the height of a bed of media particles in a column that is obtained when a consolidated or sedimented bed has been compressed, for example by contact with, and further movement of, a movable adapter or the like, or by pumping fluid through the column at a higher rate than that used during consolidation of the bed—such a bed is called a "compressed bed".

The term "compression factor" is defined as (the sedimented bed height)/(the compressed bed height) and the term "packing factor" is defined as (the consolidated bed height)/(the compressed bed height). Hereafter, when packing factor is used it should be understood that the compression factor could be used instead.

Figure 1:
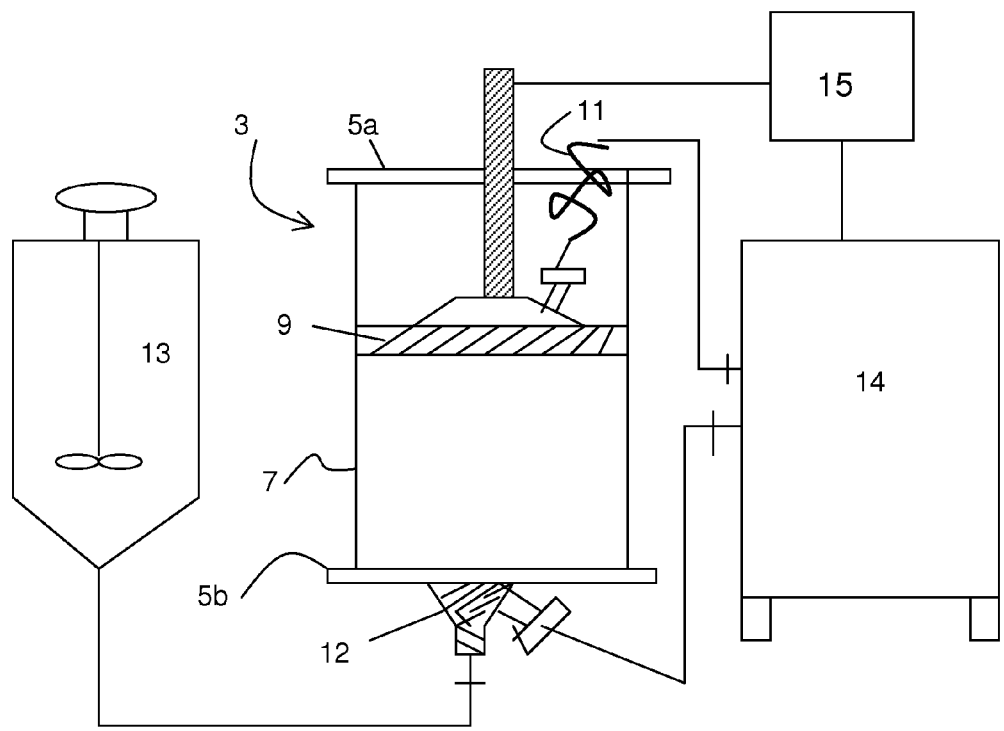
FIG. 1 is a schematic diagram of a media packing system according to the invention.

FIG. 1 is a schematic view of a column packing system according to the invention. The system comprises a column 3 which comprises upper lid or flange 5a and lower end plate 5b surrounded by a cylindrical column wall 7. Positioned between the lid or flange 5a and lower end plate 5b in the column 3 is a movable adapter 9 (which may be provided with a liquid distribution system, not shown, intended to distribute incoming liquid substantially evenly over the cross-section of the column 3, and a bed support, not shown, extending over the cross-section of the column with a mesh fine enough to prevent bed particles from passing through it) connected to a column inlet 11 connectable to a liquid delivering system 14 which delivers liquids such as sample mixtures, eluants, buffers etc. Movable adapter 9 is movable in the longitudinal direction of the column by an actuator (not shown), such as an electric, hydraulic or pneumatic motor or piston/cylinder actuator.

Slurry can be sucked into the column 3 through a nozzle or valve 12 positioned in the bottom of the column. The nozzle or valve 12 is connected to a slurry tank 13. Movable adapter 9 is provided with a positioning means (not shown) to determine the position ("x") of the movable adapter relative to a fixed level, for example the upper side of the lower end plate 5b, and a signal corresponding to the distance x is sent to a control unit 15 which in this example is connected to the liquid delivering system 14 and to the adapter actuator. The control unit 15 could however instead be built into the liquid delivering system 14. The operation of the actuator and the corresponding up or downwards movement of the movable adapter 9 is controllable by the control unit 15. Control unit 15 preferably comprises hardware and software for controlling the operation of the column 3. The control unit 15 controls for example the opening and closing of valves and the speed of the movable adapter movement. This kind of column packing systems is well known in the art and therefore all the details need not to be described here.

According to the invention the control unit 15 further comprises software for guiding the user through the packing procedure. The control unit 15 is therefore provided with or connected to some kind of display unit. The control unit 15 is furthermore provided with or connected to some kind of keyboard where the user can input data.

Figure 2:
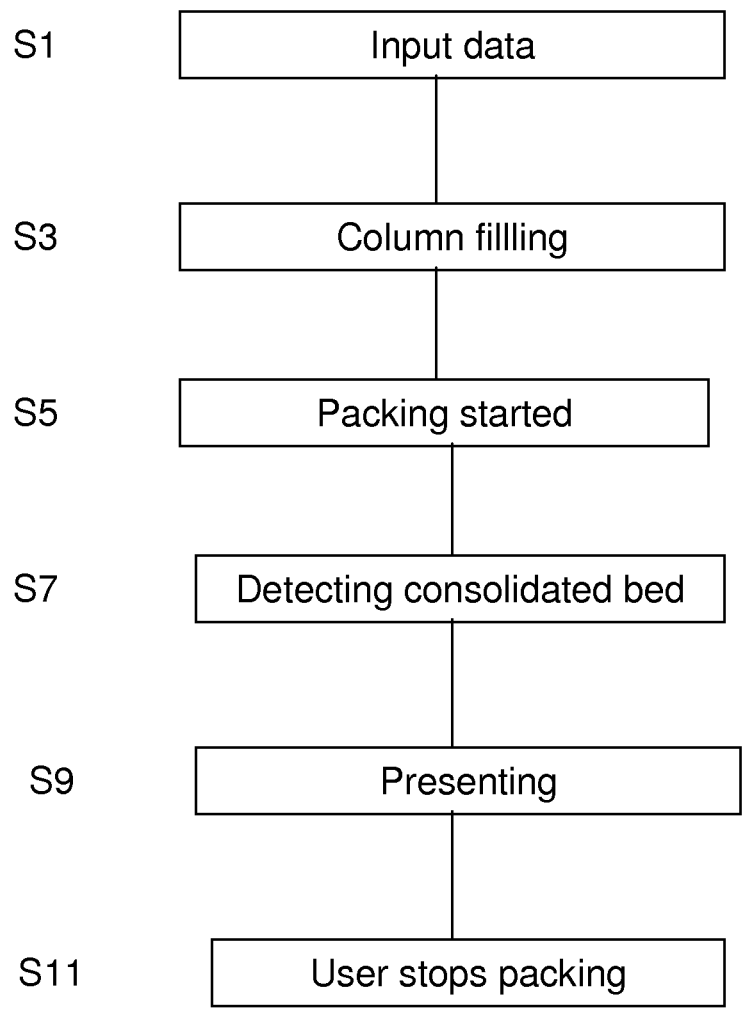
FIG. 2 is a flow chart describing the packing method according to the invention.

FIG. 2 is a flow chart of the packing process according to the invention. The steps are described below:

S1: A user provides input data to the control unit 15. These input data are in one embodiment: media type, slurry concentration (measured by the user) and target bed height preferably together with a maximum and minimum acceptable bed height. In this embodiment the control unit is provided with data related to different possible media types, i.e. given the media type from the user the control unit knows features of this media such as target packing factor (in this example we will use packing factor but compression factor could just as well have been used), preferably maximum and minimum acceptable packing factors, packing speed and filling speed suitable for this media. In another embodiment the user could also provide these input data to the control unit 15 instead of providing the media type.

S3: The control system controls the filling of the column, i.e. opens the nozzle or valve 12 and moves the adapter 9 upwards thereby sucking slurry in from the slurry tank 13. There are other possible ways of filling up the column with slurry, such as using a pump or a pressurized tank. The software in the control unit uses the input data and information of the dimensions of the column to calculate how much slurry that should be sucked into the column. Hereby, the control unit automatically fills the column (i.e. controls the movement of the adapter) with a suitable amount of slurry such that the wanted target bed height later can be achieved.

S5: The packing procedure is started, i.e. the movable adapter 9 is controlled from the control unit 15 to move downwards, i.e. towards the end plate 5b. The speed of this movement is preferably a preset value in the software of the control unit related to a chosen media type. However, in another embodiment the user could enter this data to the control unit.

S7: Detecting a consolidated bed, i.e. for example a pressure sensor provided in the column and connected to the control unit gives a signal to the control unit that the consolidated bed has been formed. This has been described before and will not be described in detail here, however the pressure in the column will change during the formation of the consolidated bed and especially when the adapter meets the bed. The consolidated bed height is an important measure as described above when the packing factor should be calculated. The consolidated bed could also be detected by measuring the motor current moving the adapter which will vary due to the varying resistance. Visual detection of the consolidated bed is also possible. Optionally, in one embodiment of the invention which will be described further in relation to FIG. 4A, the software requests a confirmation from the user that the consolidated bed has been detected to be able to ignore false detection.

S9: The software in the control unit processes the input data and the measured consolidated bed height in order to present to the user different options for when to stop the further packing of the bed. The software can illustrate to the user when the packing should be stopped for achieving an optimal packed bed given input data and measured consolidated bed height. If both target bed height and target packing factor have been given together with maximum and minimum acceptable values a window (i.e. a span of acceptable values) can be shown graphically to the user where values of the packing factor for each bed height clearly is shown. This window could for example be shown as a green area to the user (see further description in relation to FIG. 3). It could also be possible to combine the green area with a signal telling the user that if you are stopping the packing now (during the signal) the wanted conditions of the bed will be fulfilled. The user can also be shown other related data such as time until green area will be reached, time until target bed height will be reached, time to minimum bed height and so on. If either packing factor or target bed height not is accompanied by maximum and minimum acceptable values there will not be such a green area to display to the user. However the user will be shown time to target bed height (or target packing factor) and information about which packing factor (or bed height) that will be achieved and if this packing factor (or bed height) is acceptable or not.

S11: User manually stops the packing (preferably according to the recommendations given by the software in S9). However, if the packing is stopped outside the green area (or if no green area exists: in a position where the wanted conditions of the bed are not fulfilled) the software preferably shows a warning to the user. (This will be further described in relation to FIG. 4B). Furthermore, if the user does not stop the packing at all the control unit can be programmed to stop the packing itself after a predetermined period of time. This will ensure that media and/or column not will be damaged.

Figure 3:
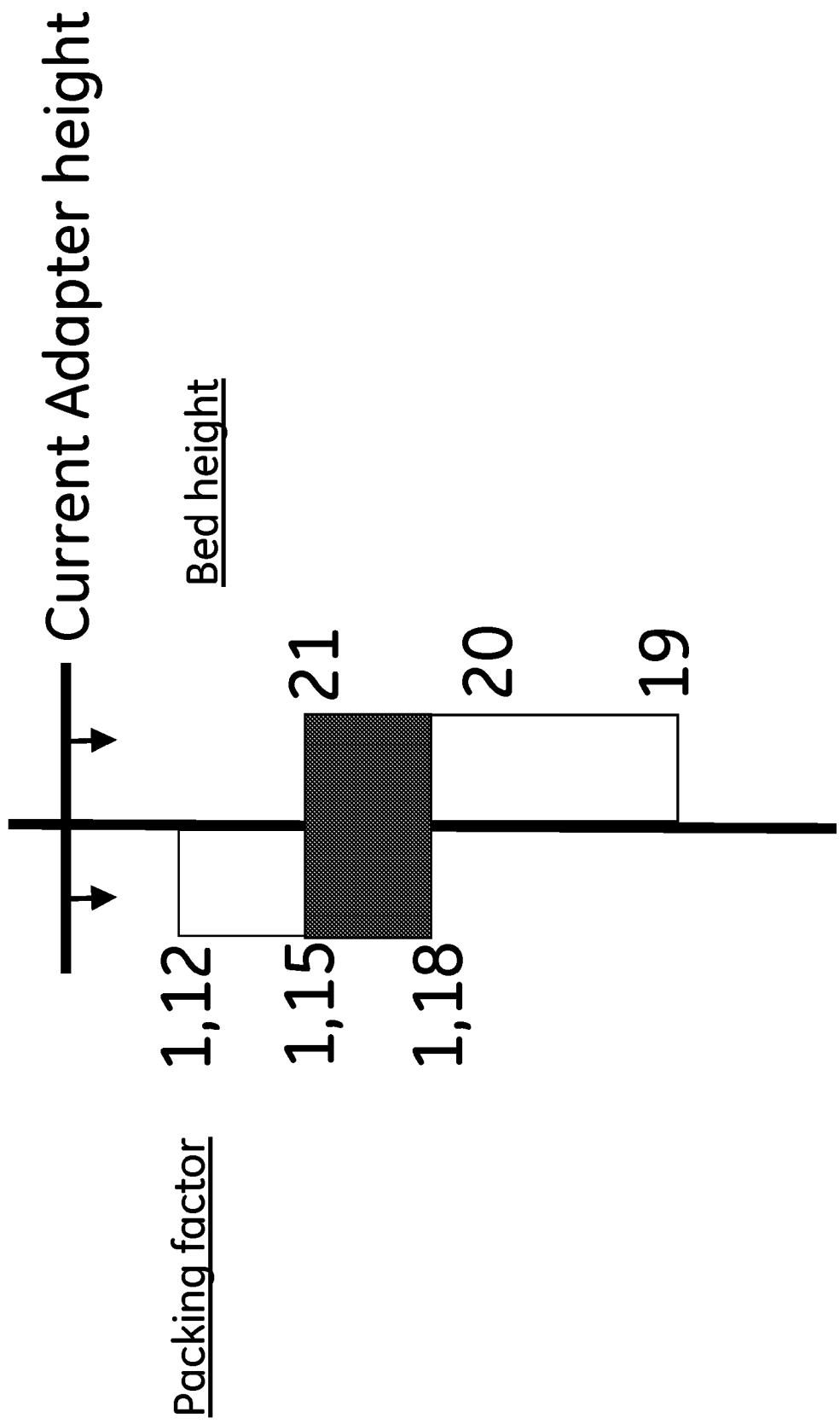
FIG. 3 is an exemplary view of a user interface according to the invention.

FIG. 3 illustrates a possible user interface according to one embodiment of the invention. In this example both target packing factor (1,15) and target bed height (20) were given together with maximum and minimum acceptable values (in this example: 1,12-1,18 and 19-21). A "green area" (the shaded area shown in FIG. 3) is then shown to the user where both packing factor and bed height are acceptable according to calculations made by the software from input data and measured consolidated bed height. Hereby the user can clearly see in which range of bed height values he can stop the packing and which packing factor he then will achieve. Other information such as time until "green area" is reached is preferably also shown to the user. In another example there is no "green area", i.e. there is no acceptable bed height where also the packing factor is acceptable. In this case the user will be informed about this and the user can decide to repack the column.

Figure 4A:
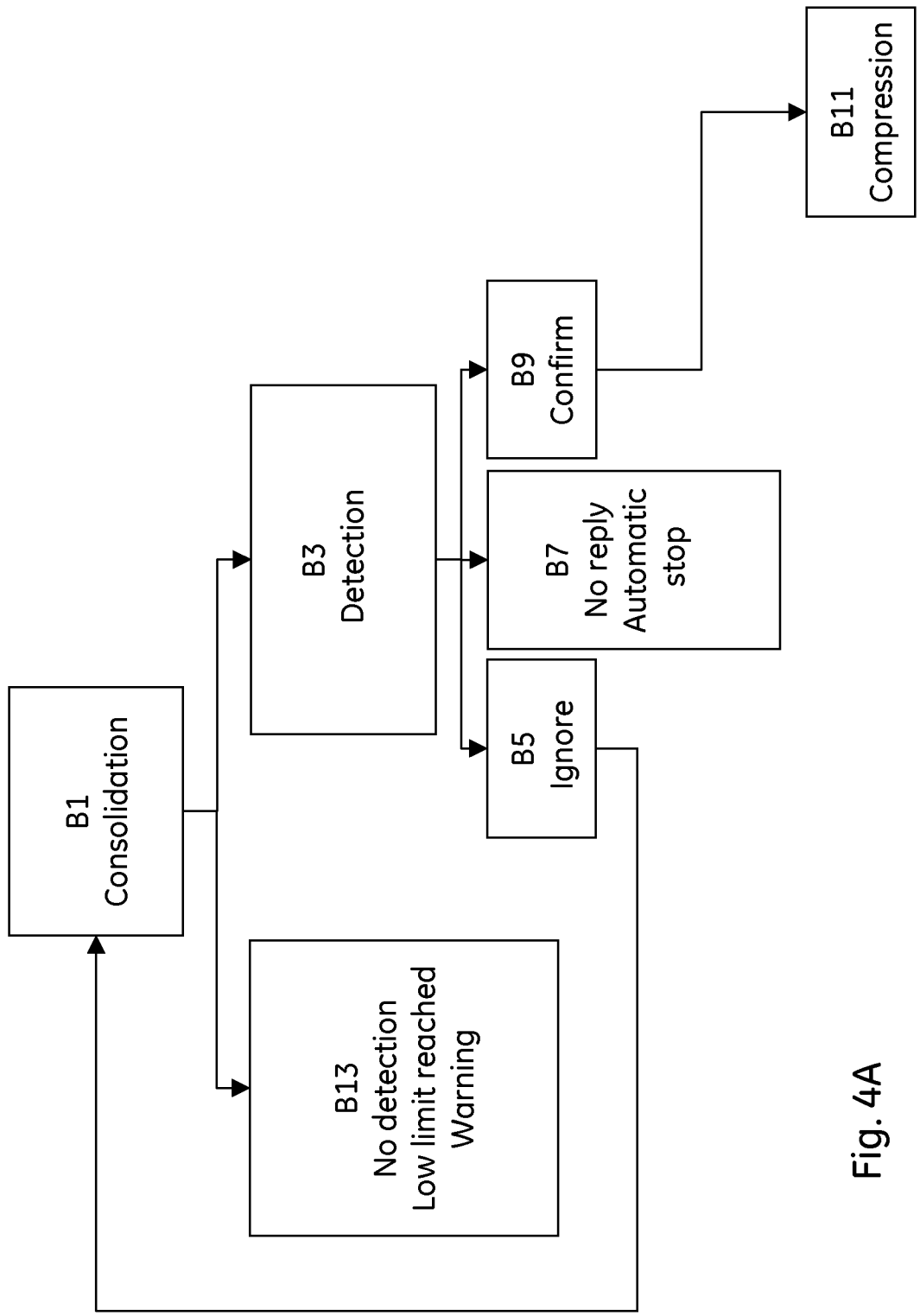
FIG. 4A is a more detailed flow chart of a consolidation process according to one embodiment of the invention.

FIG. 4A describes in more detail the step of detecting the consolidated bed according to one embodiment of the invention. The blocks are described below:

B1: The adapter is moved down and consolidation is ongoing.

B3: Consolidated bed is detected. There are different detection possibilities as described above.

B5: There should be a possibility for the user to instruct the control unit to ignore this detection because the user can see that it was a faulty detection. In this embodiment the process is simply returned to B1 waiting for next detection of consolidated bed.

B7: If the user by any reason did neither confirm nor ignore the detection the process continues to this "no reply" box and the adapter is preferably automatically stopped after a predetermined period of time. This is to ensure that the column and/or the media will not be damaged.

B9: If the user confirms the detected consolidated bed the process will proceed to compression B11 as will be further described in relation to FIG. 4B.

B13: If on the other hand no consolidated bed has been detected before a given lower limit of bed height or packing factor has been reached a warning is preferably displayed to the user and the adapter is also preferably automatically stopped such that the column and/or media will not be damaged. The user then preferably has the choice to continue or start from the beginning and maybe change some faulty input parameters.

Figure 4B:
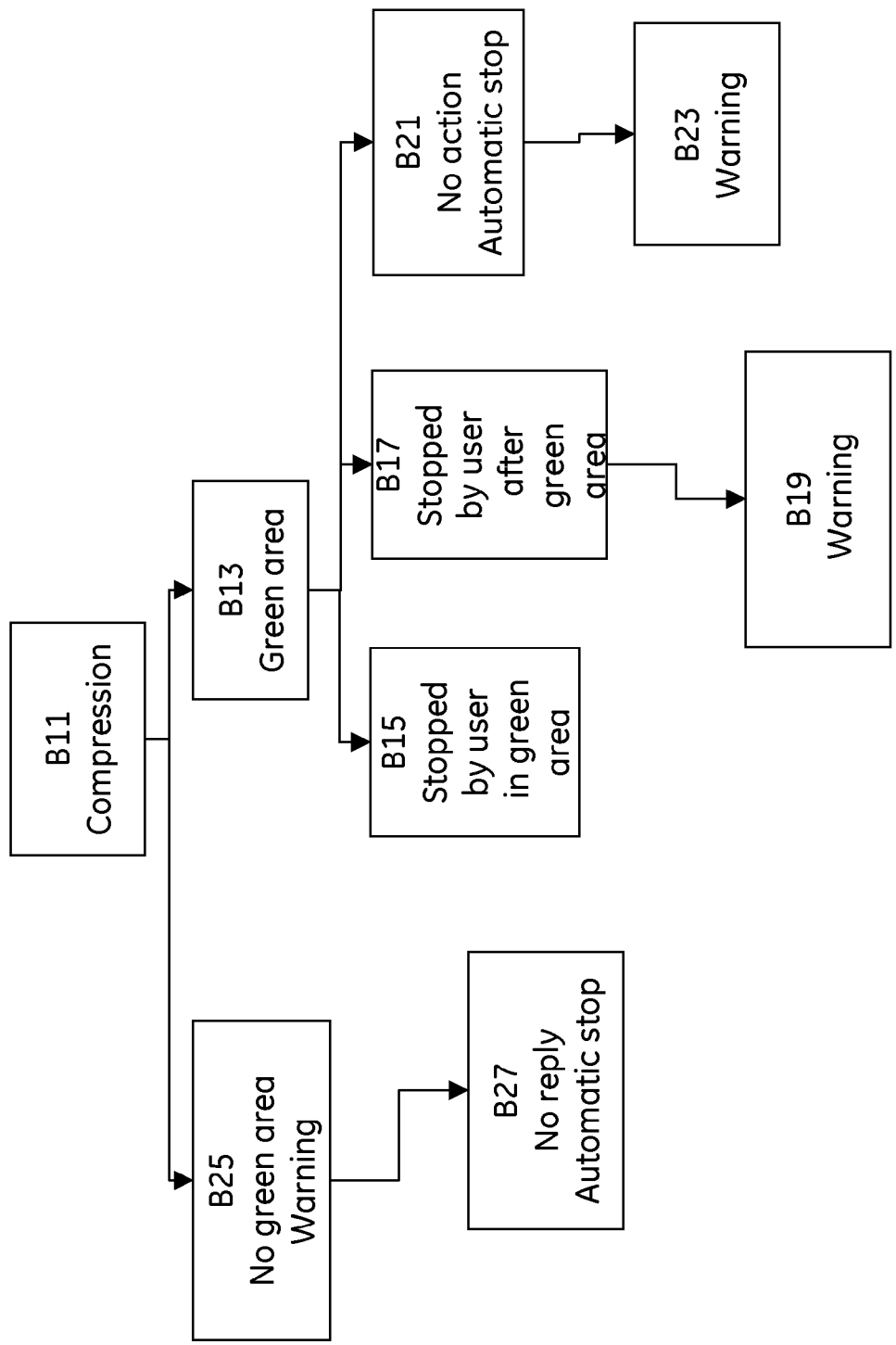
FIG. 4B is a detailed flow chart of the compression process according to one embodiment of the invention.

FIG. 4B is a more detailed description of the compression process according to one embodiment of the invention. The steps are described in order below:

B11: Compression of the consolidated bed is started. The consolidated bed height has been measured and will be used by the software in the control unit for calculations. Information is displayed to the user. In one embodiment the user interface looks like the one shown in FIG. 3 and shows a "green area". Preferably all necessary information is shown to the user including which bed height(s) will give acceptable packing factor values and preferably also information of time left until these bed heights are reached.

B13: The "green area" (as described above) is entered. Or if maximum and minimum values have only been given for one of target bed height or target packing factor the "green area" will only be a green line, i.e. a bed height value that will give a packing factor that also is acceptable or vice versa.

B15: The compression is stopped by the user within this "green area" (or correspondingly within acceptable values for both bed height and packing factor as presented to the user by the software in the control unit). Hereby the packing is completed and successful.

B17: The compression is stopped by the user after "green area" has been passed. (or correspondingly after a target value fulfilling preset conditions has been passed).

B19: In this case (B17) a warning will be displayed to the user. The warning could for example tell the user that the compression is overdone. The user can then decide if he wants to adjust the bed height manually or if the bed height still is acceptable or he can decide to repack the column.

B21: If the "green area" (or single acceptable value) is passed without the user stopping the compression the adapter is preferably automatically stopped after a predetermined period of time or after a predetermined further amount of bed compression. This is in order to avoid damaging the column and media.

B23: Also here a warning should preferably be displayed to the user telling him that the compression is overdone.

B25: Another possibility is that according to the calculations made by the software using input data and consolidated bed height there are no acceptable values of bed height where also packing factor is acceptable, i.e. no "green area". In this case a warning should be displayed to the user telling him that specifications can not be met. The user should then have the choice to stop the process or continue manually.

B27: Furthermore, if no reply is registered from the user the compression should preferably be automatically stopped after a predetermined period of time.

Although, the invention has been illustrated by examples of embodiments in which the column is cylindrical and has a constant diameter, which enables a linear correlation between cylinder volume and bed height, it is also conceivable to adapt the present invention for application to other column shapes in which the correlation is non-linear.

Even though the present invention has been described above in terms of specific embodiments, many modification and variations of this invention can be made as will be obvious to those skilled in the art, without departing from its spirit and scope as set forth in the following claims.

What is claimed is:

1. A method for packing a media bed in a column (3) from a slurry being a dispersion of said media particles and a liquid, comprising the steps of:

providing data to a control unit (15) connected to the column (3), said data comprising at least a measured slurry concentration, a target bed height, a target packing factor or compression factor and minimum and maximum acceptable values for target bed height and target packing or compression factor;

filling the column (3) with correct amount of slurry according to the column dimensions and the provided data;

forcing a movable adapter (9) along a longitudinal axis of the column (3) in order to pack the media;

detecting when the media bed is consolidated; and using the control unit (15) processing the provided data and the information about the consolidated bed height in order to present to the user acceptable bed heights, if there are any, giving acceptable packing or compression factors.

2. The method of claim 1, wherein the control unit (15) further is adapted to present to the user windows in time or distance as to when to stop the packing such that both bed height and packing or compression factor are within given acceptable ranges.

3. The method of claim 1, further comprising the step of presenting a warning to the user if no acceptable bed height values can be achieved or if the user has not stopped the packing after the minimum acceptable bed height has passed.

4. The method of claim 1, further comprising the step of controlling the packing to be automatically stopped after a predetermined period of time if no acceptable bed height values can be achieved or if the user has not stopped the packing after the minimum acceptable bed height has passed.

5. The method of claim 1, further comprising the step of user entering media type into control unit and control unit then retrieves preset values related to this specific media type from a data base for target packing or compression factor, maximum and minimum packing or compression factors and possibly also optimal speed of adapter movement during packing and optimal speed for filling the column with slurry.

6. The method of claim 1, further comprising presenting time information to the user together with the acceptable bed heights (if there are any), said time information being information about in how long time an acceptable bed height will be reached and possibly also if there is a range of acceptable bed heights how long time this acceptable region of bed heights will last during packing.

* * * * *